United States Patent [19]

Baker et al.

[11] Patent Number: 5,104,654

[45] Date of Patent: Apr. 14, 1992

[54] OVIPOSITIONAL DISRUPTION OF THE NAVEL ORANGEWORM WITH FATTY ACIDS

[75] Inventors: Thomas C. Baker, Riverside, Calif.; Paul L. Phelan, Wooster, Ohio

[73] Assignee: University of California, Alameda, Calif.

[21] Appl. No.: 446,066

[22] Filed: Dec. 5, 1989

[51] Int. Cl.$^5$ .................... A61K 35/78; A01N 25/00; C09D 5/00

[52] U.S. Cl. .................... 424/195.1; 424/84; 106/18

[58] Field of Search .................. 424/195.1, 84; 106/18

[56] References Cited

U.S. PATENT DOCUMENTS

| | | | |
|---|---|---|---|
| 2,204,009 | 3/1939 | Bruson | 106/18 |
| 2,561,379 | 7/1951 | Kalberg | 106/18 |
| 4,228,093 | 10/1980 | Carney | 556/482 |
| 4,605,560 | 8/1986 | Van Steenwyk | 424/195.1 |
| 4,639,538 | 1/1987 | Linares | 558/71 |
| 4,851,421 | 7/1989 | Iwasaki | 514/352 |

OTHER PUBLICATIONS

Reynolds, E. F. Martindale the Extra Pharmacopotia 28th Ed 1982 London, The Pharmaceutical Press p. 694, Rahway, NJ.
Almond Board of California; 1987 Annual Report, Almond Board of California Research Projects, Mar. 1988; pp. 1-2.
Almond Board of California; Almond Research Program—1988-1989, Feb. 26, 1988; pp. 1-3.
Almond Board of California; Fifteenth Annual Almond Research Conference, Dec. 1, 1987; pp. 1-2.
Almond Board of California; 1986-1987 Almond Research Progress Reports; Jun. 1987; p. 1 and Progress Report—Spring 1987; p. 1.
Almond Board of California; Almond Research Program—1987-1988; Feb. 24, 1987; pp. 1-3.
Almond Board of California; 14th Annual Almond Research Conference; Dec. 2, 1986; p. 1.
Dr. P. Larry Phelan; Navel Orangeworm Host Attractants; Progress Report Jul. 1-Dec. 31, 1986; pp. 1-7.
Almond Board of California; 1985-1986 Almond Research Progress Reports; Jun. 1986; p. 1.
Almond Board of California; 1985 Annual Report; Apr. 1986; pp. 1, 2, 6 and 7.
Almond Board of California; Almond Research Program—1986-1987; Feb. 27, 1986; pp. 1-3.
P. L. Pheland and T. C. Baker; Navel Orangeworm "Toxic Mummy" Lure and Sex Pheromone; Progress Report Jan. 1-Dec. 13, 1985; pp. 1-8.
Almond Board of California; Thirteen Annual Almond Research Conference; Dec. 3, 1985; 1985-1986 Almond Research Progress Report; pp. 1-2.

Primary Examiner—Ronald W. Griffin
Assistant Examiner—Ralph Gitomer
Attorney, Agent, or Firm—Pretty, Schroeder, Brueggemann & Clark

[57] ABSTRACT

A method and composition for the ovipositional disruption of the navel orangeworm by releasing into the air, in the area where the navel orangeworms are to be disrupted, an effective amount of a fatty acid mixture containing oleic acid and at least one other fatty acid having from 8 to 22 carbon atoms. The fatty acid mixture is preferably applied by combining at with a carrier, such as water, in the form of an emulsion which desirably contains one or more of a surfactant, a chemical slow release agent, a physical slow release agent, a UV inhibitor, or an antioxidant.

26 Claims, 6 Drawing Sheets

OVIPOSITIONAL DISRUPTION OF THE NAVEL ORANGEWORM WITH FATTY ACIDS

FIELD OF THE INVENTION

This invention relates to ovipositional disruption and attraction of insects, particularly the navel orangeworm, with fatty acid compounds.

BACKGROUND OF THE INVENTION

The navel orangeworm, Amyelois transitella, is a serious field insect pest of almonds in California resulting in the loss of millions of dollars to growers.

The female will attempt to oviposit (lay eggs) on a hullsplit nut prior to harvest or on a mummy or sticktight which is a nut which stays on the tree after harvest and cannot be dislodged. These nuts harbor overwintering pests.

Various insecticides and insect sex pheromones have been used to kill and/or disrupt communication between male and female insects and/or by ovipositonal disruption to encourage the laying of eggs on places other than the almonds. In such cases the larvae will die after hatching.

The purpose of ovipositional disruption is to release into the air one or more components of the odor of a certain object in order to make it difficult for the insect to locate that object by flying toward its odor. By releasing the disrupting agent into the air, the female is apparently unable to "smell" the object on which to oviposit, and in addition, the female may be stimulated to fly toward the artificial source(s) and lay eggs in inappropriate locations.

In U.S. Pat. No. 4,605,560, there is suggested a method and composition for the ovipositional disruption of the navel orangeworm. The method includes permeating the air or spraying almond trees with a composition of matter incorporating as an active ingredient, crude almond oil. The composition can include a water emulsion of a wettable powder formulation containing appreciably equal amounts of crude almond oil and ground almond press cake.

Crude almond oil is expressed from rejected almonds. The oil is refined and sold as a premium cooking oil. The press cake is the solid material which remains after the oil is expressed from the almonds.

The composition is applied as a spray of 5 gallons per acre crude almond oil in the form of a water emulsion.

Alternatively, 2 pounds per acre of a wettable powder formulation of crude almond oil plus almond press cake and adjuvant materials are applied as a spray.

The above application gave good suppression of egg laying and good control of larval infestations. This compares with the use of conventional insecticides as Sevin.

The patented method is desirable for use both from the standpoint of effectiveness and reduced cost compared with conventional insecticides.

However, it has been found that the application of the crude almond oil, alone or combined with almond press cake, can be phytotoxic to almond trees at certain concentrations causing the leaves to turn yellow and eventually to drop off. Moreover, the crude almond oil and the press cake have been found to contain aflatoxins which are potent carcinogens.

Accordingly, the above drawbacks have led to a search for another method for the ovipositional disruption of the navel orangeworm which has the same effectiveness but which is not phytotoxic to the almond tree at effective concentrations or contain aflatoxins.

SUMMARY OF THE INVENTION

It has now been found according to the invention that the use of free fatty acids is more effective than crude almond oil on a per weight basis as an ovipositional disruption agent when applied as a spray to almond trees. Moreover, the fatty acids do not contain aflatoxins nor are they phytotoxic to the almond trees at optimally effective dosages.

Crude almond oil contains approximately 3% of fatty acids, or about 1.5 mg in about 50 mg of oil, and is phytotoxic at effective concentrations. Crude almond oil is significantly different and must be distinguished from acidulated almond oil (AAO) which contains 100% fatty acids and is not phytotoxic at effective concentrations.

The fatty acids which are most effective according to the invention are those which are derived from natural fats and oils including animal and plant oils. Most effective are the fatty acid mixtures containing oleic, linoleic and palmitic acids, although single free fatty acids can be used with less effectiveness.

The free fatty acids or free fatty acid mixtures are preferably applied to the almond trees and/or surrounding air with a carrier, preferably water, as a water emulsion. Adjuvant materials can also be added including, among others, emulsifying agents, physical and chemical slow release agents, surfactants and the like. It has also been found that the fatty acids and fatty acid mixtures of the invention act as an attractant for the navel orangeworm and, thus, are useful as baits for insect traps.

DETAILED DESCRIPTION OF THE INVENTION

Figure 1:
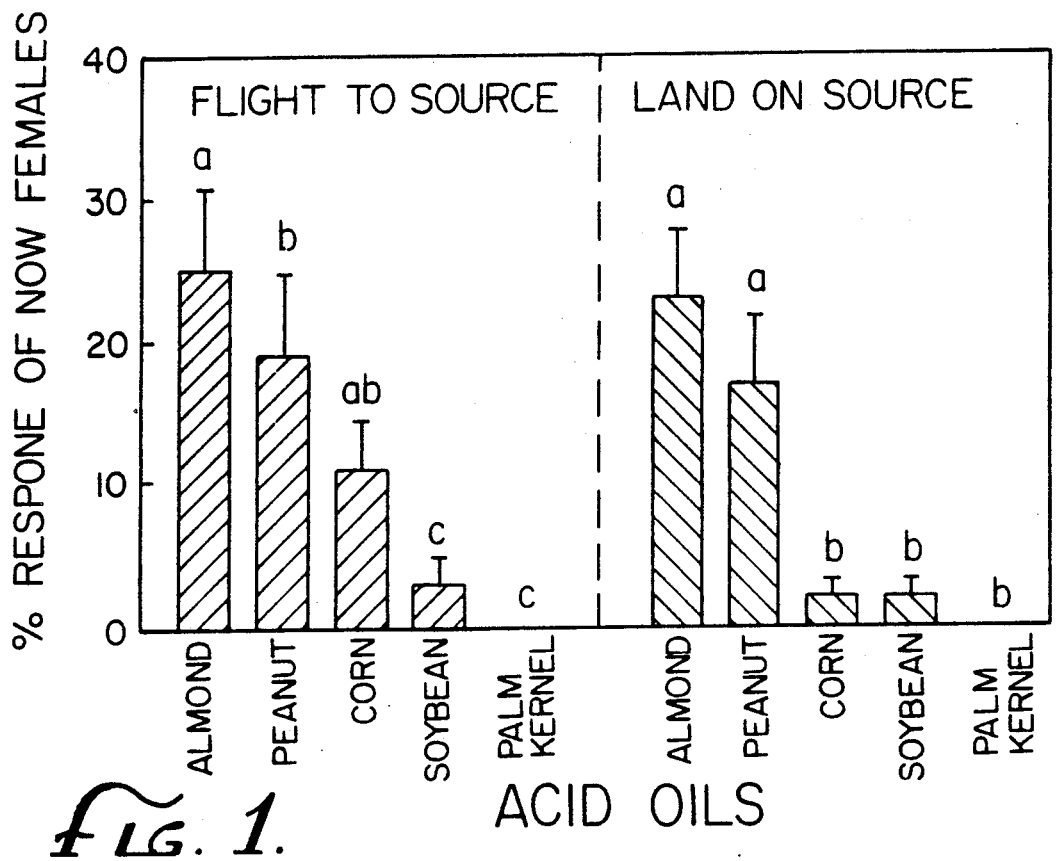
FIG. 1 shows the response of navel orangeworm (NOW) females to various acidulated oils.

The fatty acids and fatty acid mixtures useful in the invention are commonly derived from vegetable and animal oils, but can also be made synthetically. The term "fatty acid oil" refers to an oil or fat comprised predominantly of fatty acids.

During the processing of plant and animal oils and fats, it is desirable to remove the free fatty acids to avoid rancidity. This is normally done by reaction with a caustic to form a soap which permits separation from the oil. In order to free the fatty acids it is necessary to treat the soap with an acid, such as sulfuric acid.

Fats contain some fatty acids but are primarily composed of fatty acid esters with glycerol called glycerides which are readily hydrolyzed. This property is used extensively in the preparation of fatty acids. The fatty acid esters or glycerides are commonly hydrolyzed by treatment with water in the presence of caustic alkalies, alkaline earths or basic metallic oxides which act as catalysts. The products of this reaction are free fatty acids and glycerol.

Fatty acids are monobasic organic acids which are derived from natural fats and oils but can be made synthetically. Generally they have the formula $C_nH_{2n+1}COOH$. Those acids whose molecules have an even number of carbon atoms (usually 8 to 22 but can be longer or shorter in chain length) arranged in a straight chain are by far the most common and may be either saturated or unsaturated. The most abundant acids have 16 or 18 carbon atoms and these are commercially the most important.

Examples of fatty acids together with their formulas are given below. It should be understood that the invention is not limited to the examples shown.

Oleic (cis-9-octadecenoic acid) $CH_3(CH_2)_7CH:CH(CH_2)_7COOH$;
Linoleic (non-conjugated) (9,12-octadecadienoic acid) $CH_3(CH_2)_4CH:CHCH_2CH:CH(CH_2)_7COOH$;
Linoleic acid (conjugated) (9,11-octadecadienoic acid) $CH_3(CH_2)_5CH:CH(CH_2)_7COOH$;
Palmitic (hexadecanoic acid) $CH_3(CH_2)_{14}COOH$;
Stearic (n-octadecanoic acid) $CH_3(CH_2)_{16}COOH$;
Myristic (tetradecanoic acid) $CH_3(CH_2)_{12}COOH$;
Linolenic acid (9,12,15-octadecatrienoic acid) $CH_3CH_2CH:CHCH_2CH:CHCH_2CH:CH(CH_2)_7COOH$;
Arachidonic acid (5,8,11,14-eicosatetraenoic acid) $CH_3(CH_2)_4(CH:CHCH_2)_4(CH_2)_2COOH$;
Lauric acid (dodecanoic acid) $CH_3(CH_2)_{10}COOH$;
Arachidic (Eicosanoic) $C_{19}H_{39}COOH$;
Ricinoleic (12-OH,9-Octacecenoic) $C_{17}H_{33}OCOOH$;

While the free fatty acids have been found to be effective when used separately, best results have been obtained with the use of mixtures of fatty acids.

Good results have been obtained with acidulated peanut oil, with oleic or linoleic acid used separately or together, and/or in combination with palmitic acid. Oleic acid appears to be the best single fatty acid for attracting the navel orangeworm moth. Combinations of oleic and linoleic acid are the next best combination.

Most preferred is a mixture which includes among other fatty acids, oleic acid, linoleic acid and palmitic acid. The three acid mixture mentioned above combined with myristic acid also gives excellent results comparable or better than acidulated almond oil. The exact proportions of these acids do not appear to be critical. It appears that the combination has a synergistic effect when compared with the effectiveness of each of the fatty acids when used separately.

As a consequence it has been found that very pure fatty acids are not necessary. In the mixtures there are small amounts of other fatty acids and minor amounts of breakdown products of reaction between the fatty acids and reaction with air and light. The term "fatty acid" as used herein and in the appended claims, is meant to include any fatty acid breakdown products in addition to the fatty acid.

Excellent results for ovipositional disruption have been obtained using a fatty acid composition hereafter referred to as oleic acid oil containing on a weight basis 71% oleic acid, 10% linoleic acid, 6% palmitoleic acid, 6% stearic acid, 4% palmitic acid and 2% linolenic acid.

Excellent results for ovipositional attraction have also been obtained with a mixture of 4 parts by weight oleic acid, 1 part by weight linoleic and 1 part by weight palmitic acid.

Excellent results have also been obtained using acidulated almond oil and acidulated peanut oil which contain mixtures of fatty acids. Less effective results have been obtained with acidulated corn oil, and even less effective was acidulated soybean oil.

Since relatively small amounts of the fatty acids are effective, the fatty acid mixture is desirably combined with a carrier, preferably in the form of a water emulsion.

Other carriers such as oils can be used if they are not detrimental to the tree. However, as a practical matter from the standpoint of cost and availability, water is the best choice. Since fatty acids are not water soluble, an emulsifying agent and a surfactant are desirably included to provide a homogenous emulsion and to improve wetting of leaves and branches. Excellent results have been obtained using a surfactant such as Sipoteric Slip TM which is sodium lauryl imino dipropionate and an emulsifier such as Triton-100 TM.

It has been found to be desirable in order to prolong the period of effectiveness of the free fatty acids to include one or more slow release agents. Examples of slow release agents include among others: Vaporguard TM (a dimenthene polymer) and Gen-Flo-3000 TM styrene-butadiene latex polymers, and starch xanthate.

Other chemical and physical slow release agents including, among others, microencapsulates, hollow fibers, plastic laminates, porous beads and tubes and the like, can also be desirably included to further extend the period of effectiveness of the fatty acids. Other chemical and physical slow release agents besides those described above will be apparent to those skilled in the art and can be substituted for those above mentioned without departing from the invention.

Any carrier, emulsifying agent or other adjuvant materials such as UV inhibitors, anti-oxidants, chemical and physical slow release agents, used should not interfere with the effectiveness of the free fatty acids nor be detrimental to the tree or its products. The best adjuvant materials can be determined empirically among those known to those skilled in the art.

While the invention has been demonstrated effective for ovipositional disruption and attraction of navel orangeworms, it is believed that fatty acids and fatty acid mixtures might be effective for ovipositional disruption or for ovipositional attraction for other insects such as those which infest grain and other stored products.

The following examples are given for the purpose of illustrating the invention and are not intended to constitute a limitation thereof.

In the Figures and Examples, NOW refers to navel orangeworm; $p<$ refers to the probability; the numbers in parentheses (18:2) refer to the number of carbon atoms and the number of double bonds respectively in each fatty acid.

AAO refers to acidulated almond oil which contains 100% fatty acids. Acidulated almond oil is significantly different and must be distinguished from crude almond oil which contains about 3% fatty acids and is phytotoxic to almond trees in effective concentrations. This is not the case for acidulated almond oil which can be applied at upwards of 30% greater concentrations without exhibiting phytotoxicity to the almond trees.

EXAMPLES

Example 1

A field study was conducted involving approximately 30 acres of almond trees in the area of Bakersfield, Calif. to measure ovipositional disruption. The trees were divided into three blocks in which 3 acres were allocated to each treatment, along with buffer zones of ten rows of trees between treatment plots. Each block consisted of two treated plots and an untreated control plot.

Black traps for navel orangeworm eggs were placed in the trees on May 17. Egg laying was monitored throughout the period which ended just after the final harvest on September 6.

Treatments were applied during hullsplit which took place on July 13. A speed sprayer was used to apply the treatment at a rate of 40 gallons per acre diluted to provide 1.7 gallons of active ingredient per acre.

Two formulations of fatty acids were used. The base material was crude oleic acid oil which had the following fatty acid composition in percents by weight: oleic acid (71%), linoleic acid (10%), palmitoleic acid (6%), stearic acid (6%), palmitic acid (4%), and linolenic acid (2%) A water-soluble emulsion was made containing on a weight basis: 100 parts of the above oleic acid oil, 23 parts Sipoteric Slip TM, 100 parts tap water, and 2 parts Triton X-100 TM.

To this water emulsion was added two different slow release agents in order to extend the life of the oleic acid oil in the field by slowing down the rate of volatile release and by stabilizing the oil on the leaves.

Formulation 1 combined 75 gallons of the oleic oil emulsion described above with 15 gallons Vapor-Gard TM.

Formulation 2 combined 75 gallons of the oleic oil emulsion described above with 75 gallons Gen-Flo 3000 TM styrene-butadiene latex.

Both of the above concentrated formulations were diluted with water and each was applied to three 5 acre experimental plots at the rate of 40 gallons per acre by a speed sprayer operated at 22 psi and traveling 2.5 miles per hour. This amounted to 1.7 gallons of active ingredient per acre.

Examination of navel orange egg traps placed within the sprayed acres showed egg-laying was reduced by 94% for formulation 2 and 98% for Formulation 1 during the first month after application. This was particularly significant since the egg-laying in the plots treated were significantly higher prior to treatment than in the control plots. By comparison, egg-laying in the control plots declined only 15%.

Figure 10:
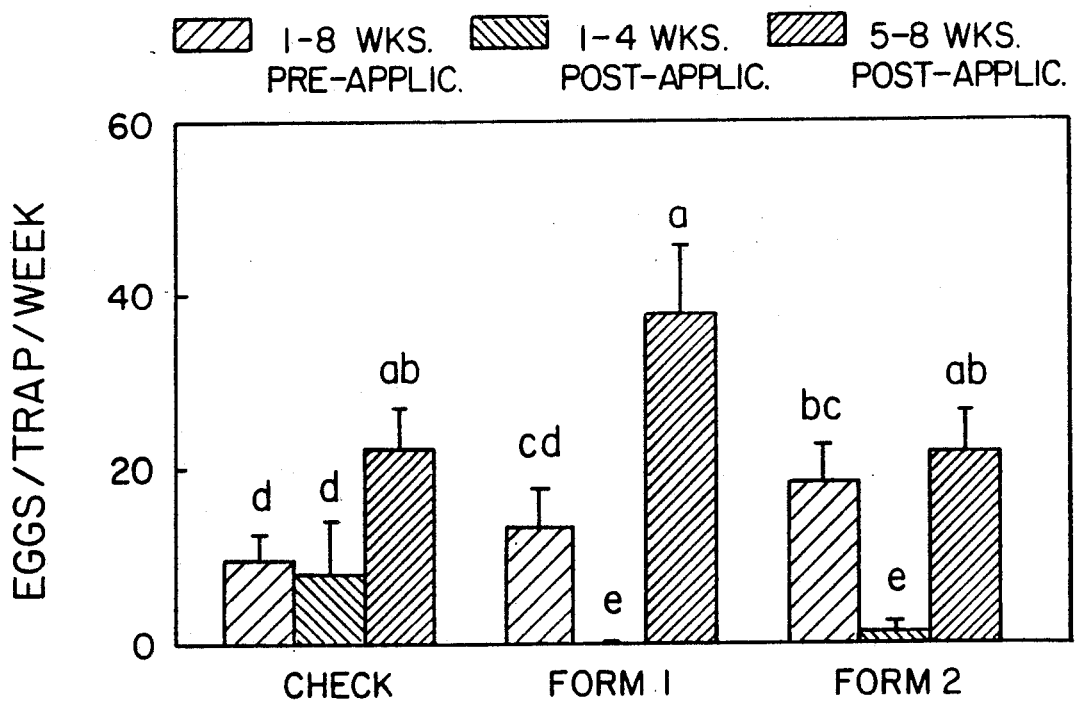
FIG. 10 shows egg-laying of NOW females on black egg traps in field plots treated with two different formulations, each containing a mixture of oleic, linoleic, palmitoleic, stearic, palmitic, and linolenic acids.

During the 2nd month, egg-laying in all plots were at or above that measured in the 8 weeks prior to the spray treatment application. This demonstrated that the extent of activity was about 4 weeks. These results can be seen in FIG. 10.

Five weeks after application, 25 nuts were sampled from ten trees in each plot and checked for navel orangeworm larval damage. Final harvest was made on September 1 which was about eight weeks after the application. At this time another nut sample was taken.

A sampling of nuts 5 weeks after spraying showed infestation by the navel orangeworm of nuts from trees sprayed with Formulation 1 were 4-fold lower than in control plots while the infestation of nuts from trees sprayed with Formulation 2 was 15-fold lower than in control plots.

Figure 11:
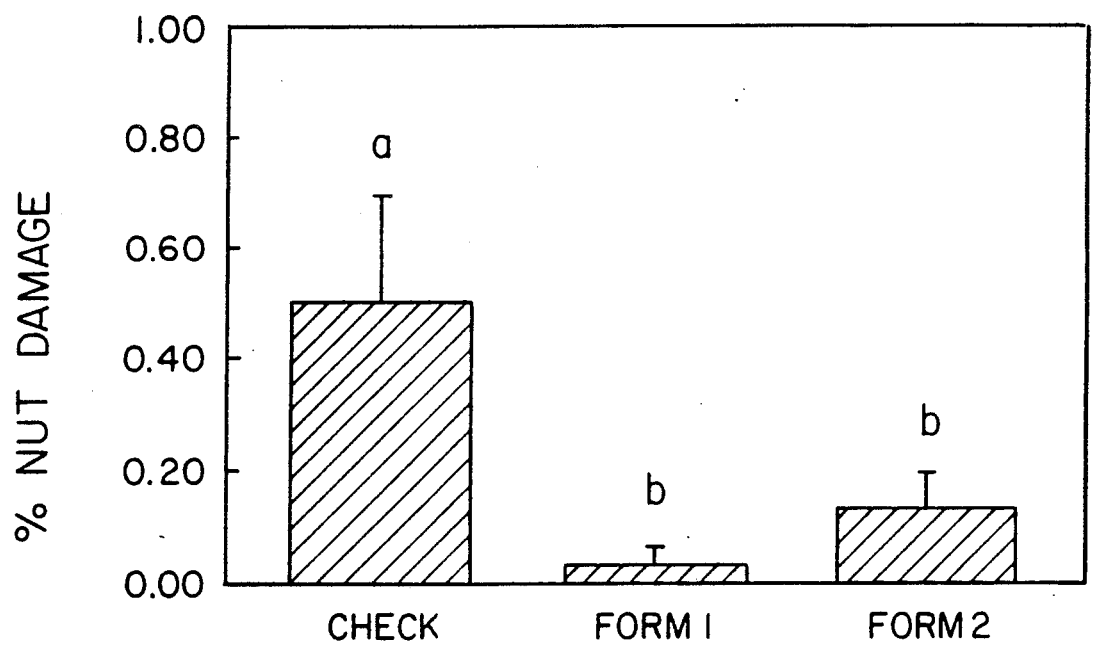
FIG. 11 shows the percent of NOW damage to nuts harvested five weeks after hullsplit in plots treated with the formulations used in FIG. 10.

At final harvest, however, infestation rates did not differ on nuts from trees sprayed with Formulation 1 or Formulation 2 and nuts from the control plot demonstrating that the effectiveness of both formulations were reduced over time. These results can be seen in FIG. 11.

Example 2

In order to investigate the ovipositional attraction by free fatty acids, a series of investigations were conducted in wind tunnels both in California and in Ohio.

The trials were conducted by putting a fatty acid in a pipette on a filter paper and placing the pipette in the upwind end of the wind tunnel. Pregnant females were then released about 2 meters downwind into the odor plume. The number of females flying up the plume and the number actually landing on the source were recorded.

Fatty acids derived from peanuts (peanut acid oil), corn,(corn acid oil), soybeans(soybean acid oil), and palm kernels,(palm kernel acid oil), were investigated and compared with the response obtained with acidulated almond oil.

The results were that in the category, "Flight to Source", including only those females that flew up the odor plume to within 5 cm of the source, the number of females showing long-distance orientation to peanut acid oil was similar to that flying to almond acid oil.

An intermediate response was obtained by corn acid oil and a minimum or no response was obtained by soybean and palm kernel acid oils.

With respect to the "Landing on Source" category, a similar pattern with 90% of females flying to the peanut acid oil actually landing on the filter paper, as compared to 88% landing on almond acid oil. These results are shown in FIG. 1.

Based on the above response it was concluded that the active ingredients found in almond acid oil were also found in peanut acid oil. At the same time it was concluded that one or more of the active constituents was lacking in the corn acid oil and soybean and palm kernel acid oils.

Figure 2:
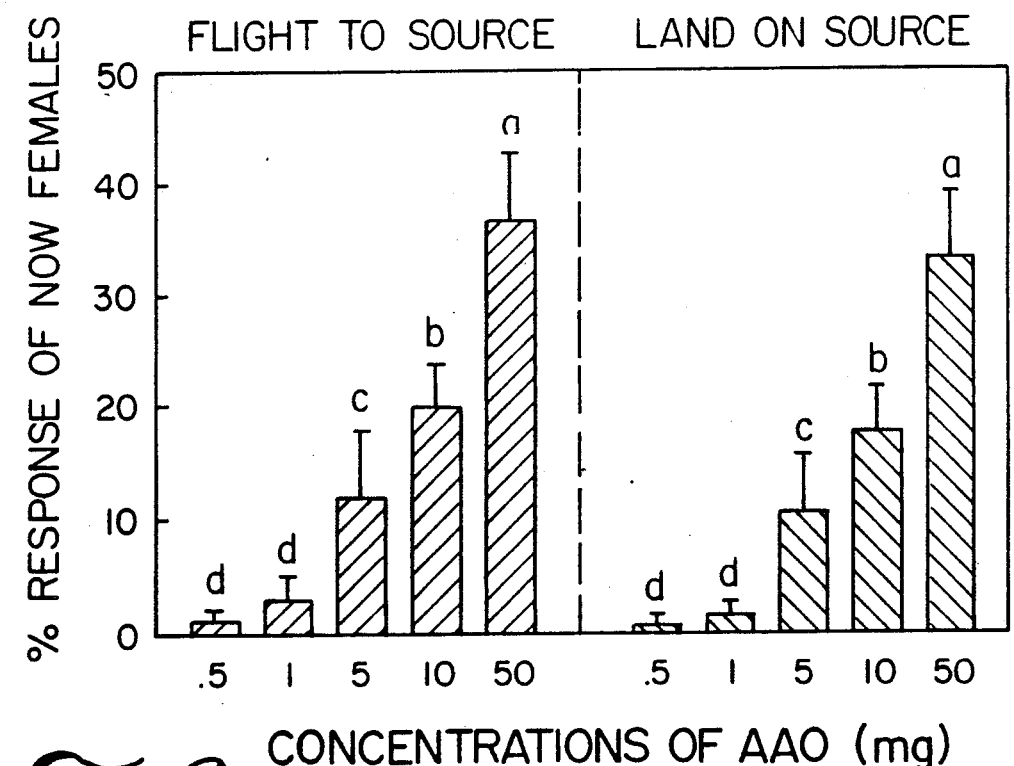
FIG. 2 shows the response of NOW females to varying concentrations of acidulated almond oil (AAO) in a wind tunnel.

It was also observed that as the concentration of acidulated almond oil was increased, the percentage of females landing increased. As expressed as a percentage of those flying up to the source, the response of females landing was approximately 91% when 5 mg, 10 mg, or 50 mg of oil was used. Thus, within the range tested, there was no evidence for premature in-flight arrestment due to higher odor concentration. These results are shown in FIG. 2.

Figure 3:
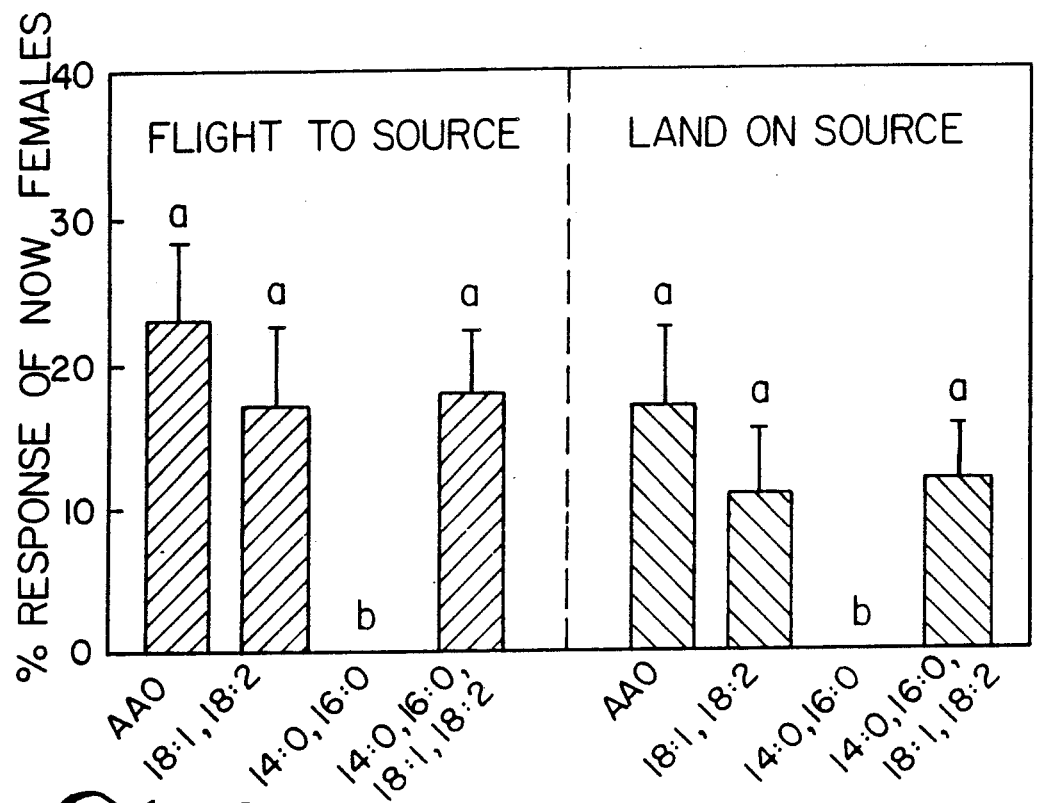
FIG. 3 shows the response of NOW females to AAO and to synthetic fatty acids.

In another wind tunnel trial, the response of NOW females to AAO, to a mixture of oleic/linoleic acids, to a mixture of palmitic/myristic acids, and to a four-acid mixture of oleic/linoleic/palmitic/myristic acids was measured. The results are shown in FIG. 3.

It was observed that both the number of females approaching to within 5cm of the source and the number landing on the source were not significantly different between acidulated almond oil and either the combination of oleic and linoleic or the mixture of all four fatty acids including oleic, linoleic, palmitic, and myristic fatty acids.

It was found that there was a non-significant trend for a lower response to both of the synthetic mixtures as compared with acidulated almond oil. The mixture of myristic and palmitic fatty acids elicited no approaches by females.

In another trial, synthetic oleic and synthetic linoleic fatty acids were tested individually, and a mixture of all four fatty acids including 38.5 mg oleic, 8.5 mg linoleic, 2.5 mg palmitic, and 0.5 mg myristic fatty acids, and a trial with 50 mg acidulated almond oil.

Figure 4:
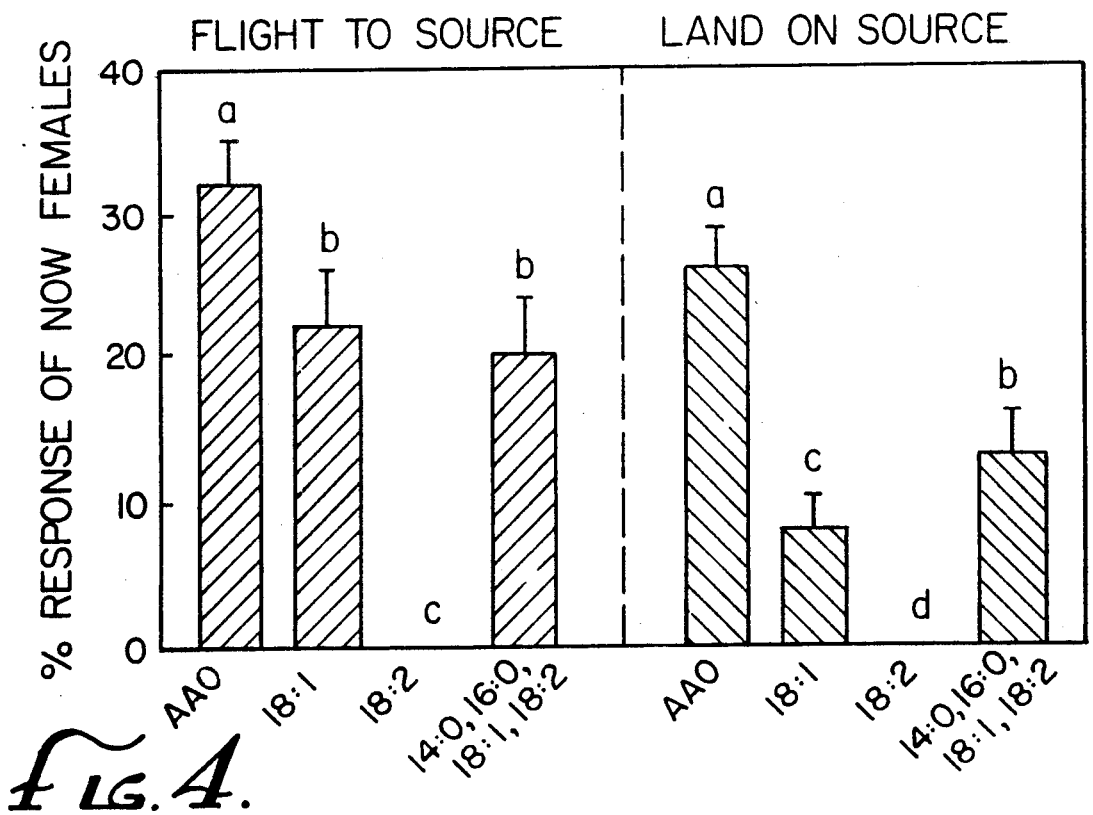
FIG. 4 shows the response of NOW females to AAO, to separate synthetic fatty acids, and to ternary synthetic fatty acid mixtures.

Oleic fatty acid alone elicited a response comparable to the oleic/linoleic fatty acid response of the previous trial. The linoleic fatty acid alone, by contrast, did not elicit any approaches. These results are shown in FIG. 4.

Based on the above it was concluded that the oleic fatty acid appeared to be responsible for female approach, the "Flight to Source" category. In the "Land on Source" category, the oleic acid was less effective. The number of females which landed on the oleic fatty acid was significantly fewer than the number of females which landed on the mixture of all four fatty acids including oleic, linoleic, palmitic, and myristic fatty acids. These results suggested that minor amounts of acids are important in increasing a short-range response.

It was also of interest that the synthetic fatty acid trial provoked significantly fewer approaches and landings than did the acidulated almond oil. This difference between the experiments may have simply been due to the fact that a larger number of replicates were administered in the second experiment, making the relationship, which is apparent in both, statistically significant in only the second experiment.

A gas chromatographic analysis of the acidulated almond oil showed the oil to be composed on a weight basis of 48% oleic, 19% palmitic, 18% linoleic, 6% palmitoleic, and 4% myristic.

Figure 5:
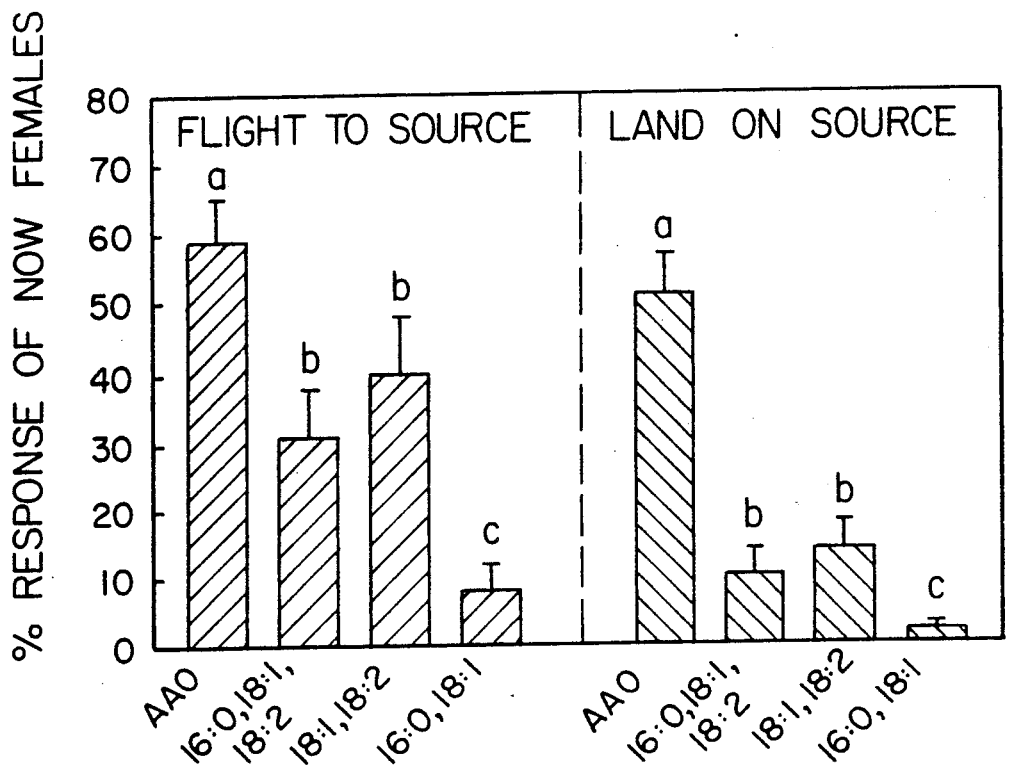
FIG. 5 shows the response of NOW females to AAO and to binary synthetic fatty acid mixtures.

Another trial was conducted using the synthetic fatty acids in the same ratios as the acidulated almond oil, namely 24 mg oleic, 10 mg palmitic, and 9 mg linoleic. The results observed were that the behavioral response was similar to the combination of oleic and linoleic in the previous trial. These results are shown in FIG. 5.

It was further noted that both the two component and three component mixtures provoked a lesser response than did the acidulated almond oil. For example, using the acidulated almond oil 87% of the females landed on the source. Using the oleic and linoleic acid mixture only 36% of approaches resulted in landings. Using the oleic/linoleic/palmitic/myristic acid mixture only 32% of the approaches resulted in landings.

Another trial was conducted to determine the effect of varying the amount of linoleic acid in combination with oleic. The concentrations of linoleic acid included 10 mg, 5 mg and 2.5 mg linoleic acid combined with 25 mg oleic acid.

Figure 6:
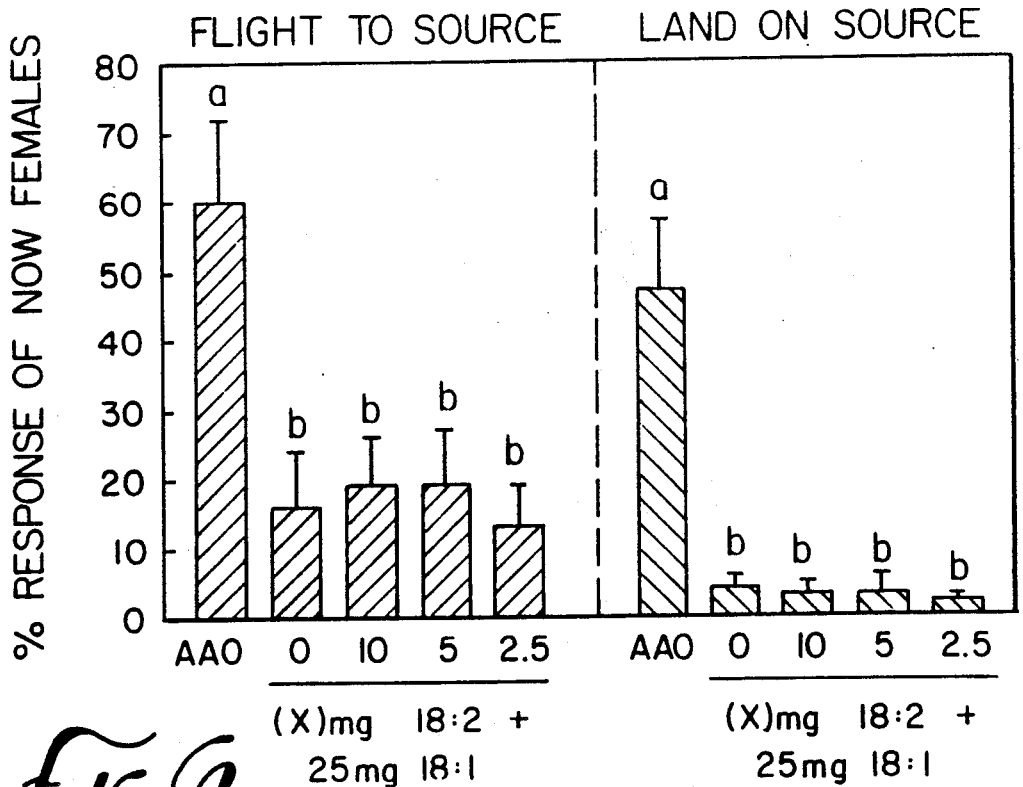
FIG. 6 shows the response of NOW females to AAO and to fatty acid mixtures including oleic acid with different concentrations of linoleic acid.

The results which are shown in FIG. 6 indicated that the addition of linoleic in any amount had no effect on either the flights to the source or on the landing rates. Also, it was observed that all the synthetic acid mixtures performed significantly lower than did the acidulated almond oil.

Figure 7:
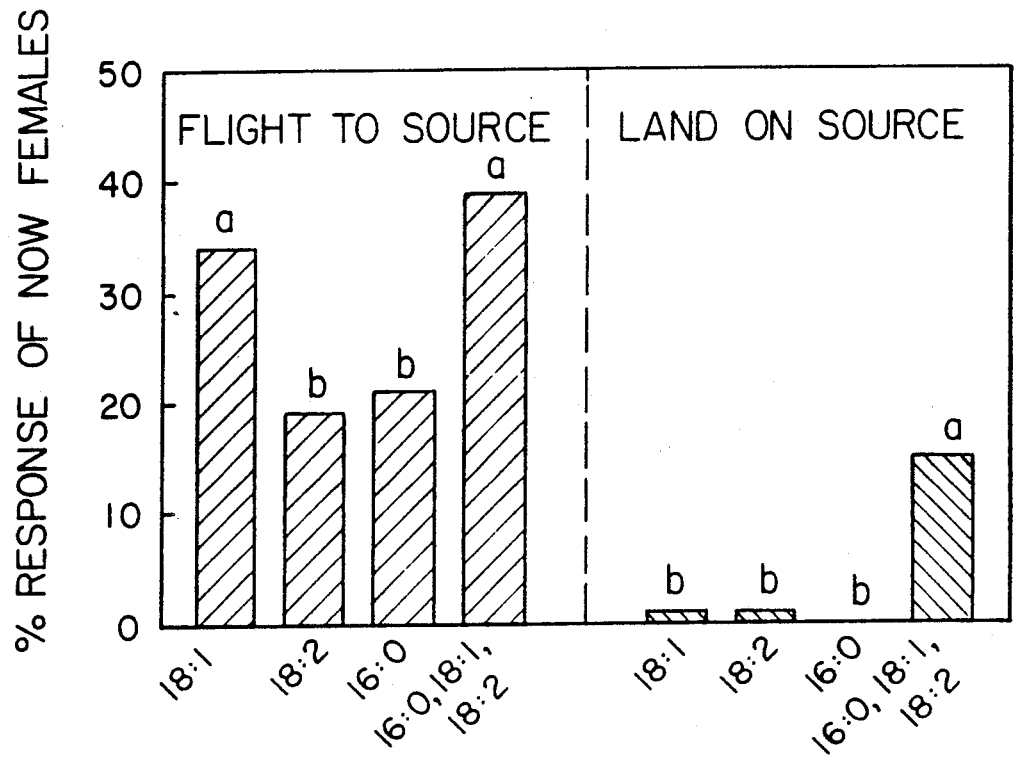
FIG. 7 shows the response of NOW females to AAO and to synthetic fatty acids tested separately and as a ternary mixture.

Another trial was conducted using a smaller wind tunnel and less chemical stimulus. First 5 mg of oleic, linoleic, and palmitic acids were tested separately. Next a mixture of the three acids in the following proportions were tested: 5 mg oleic, 1 mg linoleic, and 1 mg palmitic acid. Acidulated almond oil was also tested in the amount of 5 mg for comparison. The results are shown in FIG. 7.

The three acids tested separately were compared with the three acid mixture. It was observed that comparable numbers of females approached the oleic acid tested separately as approached the three acid mixture. Approximately half of the number of females approached the linoleic or palmitic acids when separately tested.

However, in the category of landing on the source, significantly more females responded to the three acid mixture of oleic/linoleic/palmitic acids as to any of the individual acids. Oleic acid was not significantly different from either linoleic or palmitic in this category.

Another trial was conducted to measure the differences in response between binary mixtures of oleic/palmitic; linoleic/palmitic; the individual acids tested separately; a ternary mixture of synthetic fatty acids including 5 mg oleic acid, 1 mg linoleic, and 1 mg palmitic; and acidulated almond oil.

Figure 8:
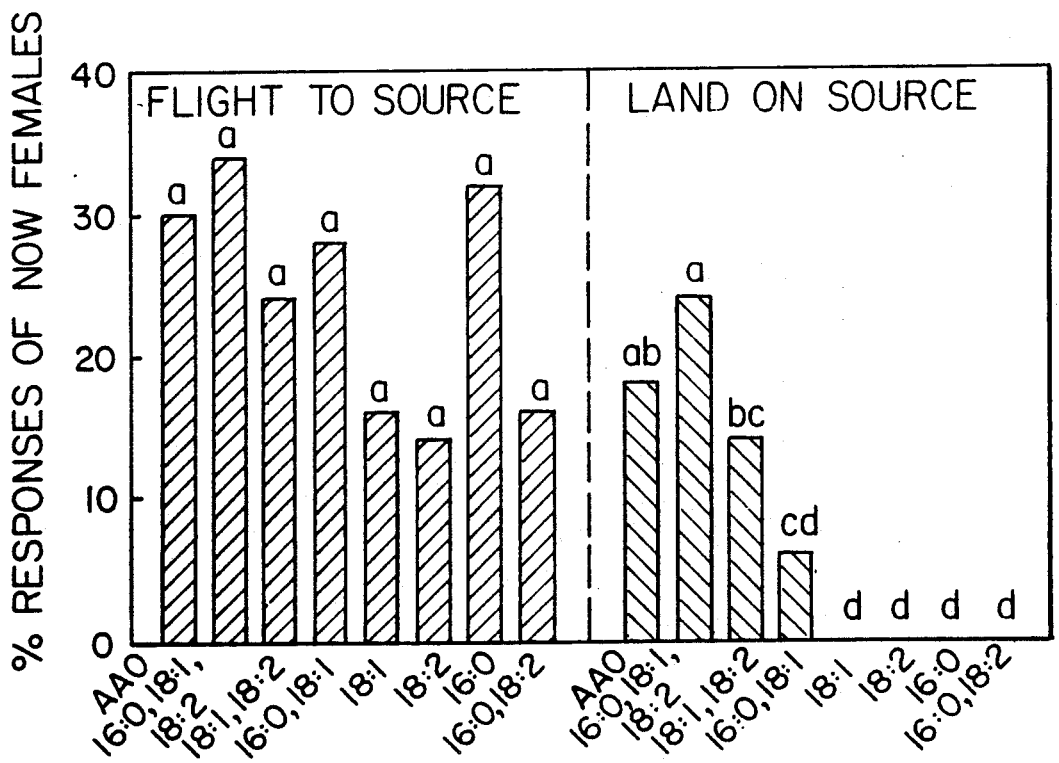
FIG. 8 shows the response of NOW females to AAO and to various fatty acids tested separately and as mixtures.

The results which are shown in FIG. 8 show no significant difference in the numbers of females approaching the odor source although the level of variability was very high. The ternary mixture of synthetic fatty acids including oleic acid, linoleic, and palmitic provoked the greatest number of females to land on the source. However, this was not significantly different from acidulated almond oil.

The combination of oleic and linoleic acids was not significantly different from acidulated almond oil but it was significantly less active than the three acid mixture.

The oleic/palmitic mixture provoked an intermediate response and the linoleic/palmitic mixture and individual acids provoked no landings.

Figure 9:
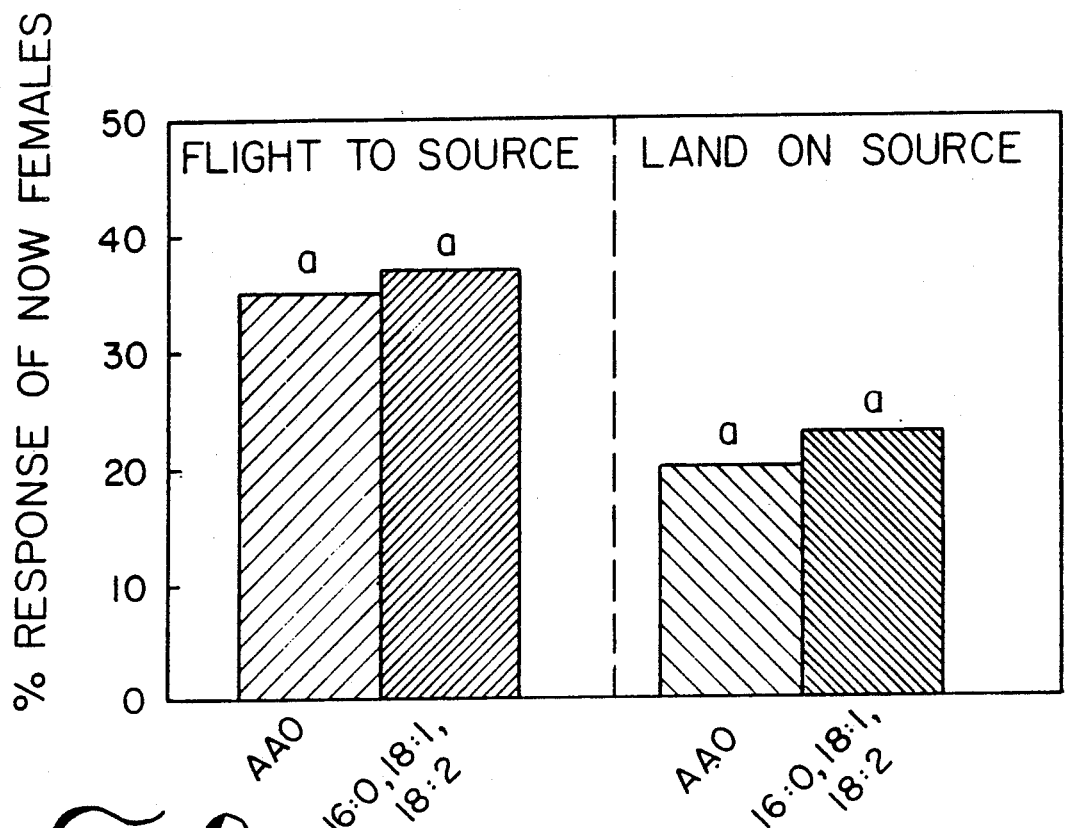
FIG. 9 shows the response of NOW females to AAO and to a mixture of synthetic oleic, linoleic and palmitic fatty acids.

A final trial was conducted in which a synthetic mixture of 2 mg oleic, 0.5 mg linoleic, and 0.1 mg palmitic acids performed similarly to 5 mg acidulated almond oil in both approaches and landings by females. These results are shown in FIG. 9.

As a result of the above experiments, it is thought that oleic acid is the best single fatty acid in the category of "Flight to Source". The combination of oleic and linoleic acid is comparable.

Various modifications of the invention as above described will be obvious to those skilled in the art and can be resorted to without departing from the spirit and scope of the invention as defined in the following claims.

We claim:

1. A method for obtaining ovipositional disruption of naval orangeworms comprising:
   releasing into the air, in the area where the egg-laying by the naval orangeworms is to be disrupted, an effective amount of a fatty acid mixture comprising a major amount of oleic acid and at least one other fatty acid having from 8 to 22 carbon atoms.

2. A method as claimed in claim 1 further comprising the step of combining said fatty acid mixture with a carrier prior to the step of releasing said mixture into the air.

3. A method as claimed in claim 2 wherein said carrier is water.

4. A method as claimed in claim 3 wherein said fatty acid mixture and said water are in the form of an emulsion.

5. A method as claimed in claim 4 further comprising the step of combining the emulsion with a slow release agent prior to the step of releasing said mixture into the air.

6. A method as claimed in claim 5 wherein the fatty acid mixture comprises a major amount of oleic acid and at least one other fatty acid selected from the group consisting of linoleic acid, palmitic acid, myristic acid, stearic acid, linolenic acid, and palmitoleic acid.

7. A method as claimed in claim 4 wherein the fatty acid mixture comprises a major amount of oleic acid and at least one other fatty acid selected from the group consisting of linoleic acid, palmitic acid, myristic acid, stearic acid, linolenic acid, and palmitoleic acid.

8. A method as claimed in claim 1 further comprising breakdown products of said fatty acids.

9. A method as claimed in claim 1 wherein said fatty acid mixture includes linoleic acid.

10. A method as claimed in claim 1 wherein said fatty acid mixture includes palmitic acid.

11. A method as claimed in claim 1 wherein said fatty acid mixture includes myristic acid.

12. A method as claimed in claim 1 wherein there are at least two other fatty acids selected from the group consisting of linoleic acid, palmitic acid, myristic acid, stearic acid, linolenic acid, and palmitoleic acid.

13. A method as claimed in claim 12 wherein the fatty acid mixture is emulsified in water.

14. A method as claimed in claim 13 further comprising the step of combining the emulsion with a slow release agent prior to the step of releasing said mixture into the air.

15. A method as claimed in claim 12 further comprising the step of combining the fatty acid mixture with a slow release agent prior to the step of releasing said mixture into the air.

16. A method as claimed in claim 1 further comprising the step of combining the fatty acid mixture with a slow release agent prior to the step of releasing said mixture into the air.

17. A method as claimed in claim 16 wherein the fatty acid mixture comprises a major amount of oleic acid and at least one other fatty acid selected from the group consisting of linoleic acid, palmitic acid, myristic acid, stearic acid, linolenic acid, and palmitoleic acid.

18. A method for obtaining ovipositional disruption of naval orangeworms comprising:

releasing into the air, in the area where the egg-laying by the naval orangeworms is to be disrupted, an effective amount of a fatty acid mixture comprising a major amount of oleic acid, linoleic acid, at least one other fatty acid having from 8 to 22 carbon atoms, and at least one additional compound selected from the group consisting of chemical slow release agents, physical slow release agents, surfactants, emulsifying agents, antioxidants, and UV absorbers.

19. A method as claimed in claim 18 wherein said fatty acid mixture comprises 71% oleic acid, 10% linoleic acid, 6% palmitoleic acid, 6% stearic acid, 4% palmitic acid, and 2% linolenic acid.

20. A method as claimed in claim 19 wherein said fatty acid mixture in the form of a water emulsion comprises 100 parts by weight of said fatty acids, 100 parts by weight water, 23 parts by weight of a surfactant, and 2 parts by weight of an emulsifying agent.

21. A method as claimed in claim 20 wherein 75 parts of said fatty acid mixture in the form of a water emulsion is combined with 15 parts of a dimenthene polymer.

22. A method as claimed in claim 20 wherein 75 parts of said fatty acid mixture in the form of a water emulsion is combined with 15 parts of a styrene-butadiene latex polymer.

23. A method as claimed in claim 18 wherein said fatty acid mixture comprises 4 parts by weight oleic acid, one part by weight linoleic acid, and one part by weight palmitic acid.

24. A method as claimed in claim 18 wherein the fatty acid mixture includes palmitic acid.

25. A method as claimed in claim 18 wherein the fatty acid mixture includes myristic acid.

26. A method as claimed in claim 18 wherein said fatty acid mixture further includes palmitic acid and myristic acid.

* * * * *

UNITED STATES PATENT AND TRADEMARK OFFICE
CERTIFICATE OF CORRECTION

PATENT NO. : 5,104,654
DATED : April 14, 1992
INVENTOR(S) : Thomas C. Baker, et al It is certified that error appears in the above-indentified patent and that said Letters Patent is hereby corrected as shown below:

On the title page, In OTHER PUBLICATIONS, Line 3:

"Rahway, NJ." should be -- The Merck Index 11th Ed 1989, Merck & Co., Rahway, NJ. --.

Column 1, line 61: "cake." should be -- cake --.

Column 3, line 61: "oleic acid" should be -- Oleic acid --.

Column 5, line 66: "formulation 2" should be -- Formulation 2 --.

Signed and Sealed this

Thirty-first Day of August, 1993

Attest:

BRUCE LEHMAN

Attesting Officer      Commissioner of Patents and Trademarks